US009763992B2

(12) United States Patent
Walsh

(10) Patent No.: US 9,763,992 B2
(45) Date of Patent: Sep. 19, 2017

(54) TREATMENT OF NOISE INDUCED HEARING LOSS

(71) Applicant: Father Flanagan's Boys' Home, Omaha, NE (US)

(72) Inventor: Edward J. Walsh, Omaha, NE (US)

(73) Assignee: Father Flanagan's Boys' Home, Omaha, NE (US)

( * ) Notice: Subject to any disclaimer, the term of this patent is extended or adjusted under 35 U.S.C. 154(b) by 84 days.

(21) Appl. No.: 14/621,978

(22) Filed: Feb. 13, 2015

(65) Prior Publication Data

US 2015/0224163 A1    Aug. 13, 2015

Related U.S. Application Data

(60) Provisional application No. 61/939,362, filed on Feb. 13, 2014.

(51) Int. Cl.
| | | |
|---|---|---|
| *A61K 38/02* | (2006.01) | |
| *A61K 31/221* | (2006.01) | |
| *A61K 31/225* | (2006.01) | |
| *A61K 31/198* | (2006.01) | |
| *A61K 38/00* | (2006.01) | |
| *A61K 9/00* | (2006.01) | |

(52) U.S. Cl.
CPC ............ *A61K 38/02* (2013.01); *A61K 31/198* (2013.01); *A61K 31/221* (2013.01); *A61K 31/225* (2013.01); *A61K 38/00* (2013.01); *A61K 9/0046* (2013.01)

(58) Field of Classification Search
CPC ....... A61K 38/00; A61K 38/02; A61K 9/0046
See application file for complete search history.

(56) References Cited

U.S. PATENT DOCUMENTS

| | | | |
|---|---|---|---|
| 7,718,702 B2 | 5/2010 | Kozlowski et al. | |
| 8,299,128 B2 | 10/2012 | Sill et al. | |
| 8,399,413 B2 | 3/2013 | Klinger | |
| 2003/0077641 A1 | 4/2003 | Laskowitz et al. | |
| 2004/0009169 A1 | 1/2004 | Taylor et al. | |
| 2004/0053953 A1 | 3/2004 | Taveras et al. | |
| 2004/0186142 A1 | 9/2004 | Taveras et al. | |
| 2005/0064483 A1 | 3/2005 | Zang et al. | |
| 2005/0192345 A1 | 9/2005 | Hu et al. | |
| 2006/0013905 A1 | 1/2006 | Tehoharides | |
| 2006/0014794 A1 | 1/2006 | Chao et al. | |
| 2006/0025453 A1 | 2/2006 | Taveras et al. | |
| 2006/0173053 A1 | 8/2006 | Shinitzky et al. | |
| 2006/0217392 A1 | 9/2006 | Anilkumar et al. | |
| 2006/0223864 A1 | 10/2006 | Biju et al. | |
| 2006/0276448 A1 | 12/2006 | Zeng et al. | |
| 2006/0276457 A1 | 12/2006 | Yu et al. | |
| 2006/0276479 A1 | 12/2006 | Kim et al. | |
| 2006/0276480 A1 | 12/2006 | Wong et al. | |
| 2007/0021611 A1 | 1/2007 | McGuinness et al. | |
| 2007/0054919 A1 | 3/2007 | Rosenblum et al. | |
| 2007/0082841 A1 | 4/2007 | Higuchi et al. | |
| 2007/0155756 A1 | 7/2007 | Taveras et al. | |
| 2007/0202077 A1 | 8/2007 | Brodsky et al. | |
| 2007/0248594 A1 | 10/2007 | Chao et al. | |
| 2007/0264230 A1 | 11/2007 | Taveras et al. | |
| 2008/0039474 A1 | 2/2008 | Rosenblum et al. | |
| 2008/0045489 A1 | 2/2008 | Chao et al. | |
| 2008/0058343 A1 | 3/2008 | Rosenblum et al. | |
| 2008/0090823 A1 | 4/2008 | Biju et al. | |
| 2008/0161361 A1 | 7/2008 | Wu et al. | |
| 2008/0279822 A1 | 11/2008 | Hu et al. | |
| 2008/0292589 A1 | 11/2008 | Anilkumar et al. | |
| 2009/0068143 A1 | 3/2009 | Yacovan et al. | |
| 2009/0098086 A1 | 4/2009 | Zask et al. | |
| 2009/0149458 A1 | 6/2009 | Chen et al. | |
| 2009/0149541 A1 | 6/2009 | Stark et al. | |
| 2009/0227575 A1 | 9/2009 | Venkatesan et al. | |
| 2009/0291079 A1 | 11/2009 | Venkatesan et al. | |
| 2009/0297477 A1 | 12/2009 | Voskuhl | |
| 2009/0298820 A1 | 12/2009 | Tsou et al. | |
| 2009/0304692 A1 | 12/2009 | Venkatesan et al. | |
| 2009/0311217 A1 | 12/2009 | Bursavich et al. | |
| 2010/0003250 A1 | 1/2010 | Chen et al. | |
| 2010/0015141 A1 | 1/2010 | Bursavich et al. | |
| 2010/0015235 A1 | 1/2010 | Watson et al. | |
| 2010/0028441 A1 | 2/2010 | Watson et al. | |
| 2010/0040537 A1 | 2/2010 | Gu et al. | |
| 2010/0061982 A1 | 3/2010 | Ayral-Kaloustian et al. | |
| 2010/0068204 A1 | 3/2010 | Tsou et al. | |
| 2010/0150868 A1 | 6/2010 | Achiron et al. | |
| 2010/0168124 A1 | 7/2010 | Rosenblum et al. | |

(Continued)

FOREIGN PATENT DOCUMENTS

| | | |
|---|---|---|
| EP | 1778676 B1 | 8/2010 |
| EP | 2295071 A1 | 3/2011 |

(Continued)

OTHER PUBLICATIONS

Campbell et al., "Prevention of noise- and drug-induced hearing loss with D-methionine," *Hear Res*, 2007; 226(1-2):92-103.
Carpintero et al., "Glatiramer acetate triggers PI3Kδ/Akt and MEK/ERK pathways to induce IL-1 receptor antagonist in human monocytes," *Proc Natl Acad Sci USA*, 2010; 107:17692-17697.
Choi et al., "Effectiveness of 4-hydroxy phenyl N-tert-butylnitrone (4-OHPBN) alone and in combination with other antioxidant drugs in the treatment of acute acoustic trauma in chinchilla," *Free Radic Biol Med*, 2008; 44:1772-1784.
"Copaxone (Glatiramer Acetate) Drug Information," RxList The Internet Drug Index, 2014. Retrieved from the Internet on Feb. 12, 2014: <URL: http://www.rxlist.com/script/main/rxlist.asp?articlekey=69568&pf=3&page=1>; 2 pages.

(Continued)

*Primary Examiner* — Robert C Hayes
(74) *Attorney, Agent, or Firm* — Mueting, Raasch & Gebhardt, P.A.

(57) ABSTRACT

The present invention provides methods of preventing, treating, and/or reducing noise induced hearing loss and/or noise-induced inner ear trauma. The methods include the administration of glatiramer acetate or a derivative thereof and, optionally, at least one anti-oxidant.

20 Claims, 7 Drawing Sheets

(56) References Cited

U.S. PATENT DOCUMENTS

| | | |
|---|---|---|
| 2010/0305023 A1 | 12/2010 | Stark et al. |
| 2010/0310609 A1 | 12/2010 | Watson et al. |
| 2011/0046065 A1 | 2/2011 | Klinger |
| 2011/0052535 A1 | 3/2011 | Foussat et al. |
| 2011/0091534 A1 | 4/2011 | Breitenkamp et al. |
| 2011/0123482 A1 | 5/2011 | Kaplin et al. |
| 2011/0212053 A1 | 9/2011 | Qian et al. |
| 2011/0311483 A1 | 12/2011 | Jia et al. |
| 2012/0014915 A9 | 1/2012 | Voskuhl |
| 2012/0039958 A1 | 2/2012 | Watson et al. |
| 2012/0121656 A1 | 5/2012 | Watson et al. |
| 2012/0263764 A1 | 10/2012 | Watson |
| 2012/0329758 A1 | 12/2012 | Cohen et al. |
| 2013/0005723 A1 | 1/2013 | Venkatesan et al. |
| 2013/0165387 A1 | 6/2013 | Klinger |
| 2013/0225525 A1 | 8/2013 | Cohen et al. |

FOREIGN PATENT DOCUMENTS

| | | |
|---|---|---|
| EP | 2324851 A1 | 5/2011 |
| EP | 2332565 A1 | 6/2011 |
| EP | 1858888 B1 | 4/2013 |
| WO | WO 01/42219 A2 | 6/2001 |
| WO | WO 03/026479 A2 | 4/2003 |
| WO | WO 03/080053 A1 | 10/2003 |
| WO | WO 2004/032824 A2 | 4/2004 |
| WO | WO 2004/033440 A1 | 4/2004 |
| WO | WO 2005/066147 A1 | 7/2005 |
| WO | WO 2005/068460 A1 | 7/2005 |
| WO | WO 2005/075447 A1 | 8/2005 |
| WO | WO 2005/113534 A2 | 12/2005 |
| WO | WO 2006/043260 A2 | 4/2006 |
| WO | WO 2006/088836 A2 | 8/2006 |
| WO | WO 2006/088837 A2 | 8/2006 |
| WO | WO 2006/088840 A1 | 8/2006 |
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2006/100673 A2 | 9/2006 |
| WO | WO 2006/102170 A2 | 9/2006 |
| WO | WO 2007/038435 A2 | 4/2007 |
| WO | WO 2007/038687 A2 | 4/2007 |
| WO | WO 2007/109238 A1 | 9/2007 |
| WO | WO 2008/005570 A1 | 1/2008 |
| WO | WO 2008/008453 A1 | 1/2008 |
| WO | WO 2008/079279 A1 | 7/2008 |
| WO | WO 2008/149354 A2 | 12/2008 |
| WO | WO 2008/156494 A1 | 12/2008 |
| WO | WO 2009/027105 A2 | 3/2009 |
| WO | WO 2009/045464 A1 | 4/2009 |
| WO | WO 2009/052145 A1 | 4/2009 |
| WO | WO 2009/070298 A1 | 6/2009 |
| WO | WO 2009/070524 A1 | 6/2009 |
| WO | WO 2009/111547 A1 | 9/2009 |
| WO | WO 2009/132939 A1 | 11/2009 |
| WO | WO 2009/134728 A2 | 11/2009 |
| WO | WO 2009/143313 A1 | 11/2009 |
| WO | WO 2009/143317 A1 | 11/2009 |
| WO | WO 2009/155042 A1 | 12/2009 |
| WO | WO 2009/155052 A1 | 12/2009 |
| WO | WO 2009/155527 A2 | 12/2009 |
| WO | WO 2010/002954 A1 | 1/2010 |
| WO | WO 2010/006059 A1 | 1/2010 |
| WO | WO 2010/011620 A1 | 1/2010 |
| WO | WO 2010/030727 A1 | 3/2010 |
| WO | WO 2010/030967 A1 | 3/2010 |
| WO | WO 2010/043561 A2 | 4/2010 |
| WO | WO 2011/022063 A1 | 2/2011 |
| WO | WO 2011/083467 A1 | 7/2011 |
| WO | WO 2011/137317 A1 | 11/2011 |
| WO | WO 2012/021856 A1 | 2/2012 |
| WO | WO 2012/142501 A1 | 10/2012 |

OTHER PUBLICATIONS

Fujioka et al., "Proinflammatory cytokines expression in noise-induced damaged cochlea," *JNeurosci Res*, 2006; 83:575-583.

Gentile et al., "Glatiramer acetate protects against inflammatory synaptopathy in experimental autoimmune encephalomyelitis," *J Neuroimmune Pharmacol*, 2013; 8:651-663.

Henderson et al., "The role of oxidative stress in noise-induced hearing loss," *Ear Hear*, 2006; 27:1-19.

Humes et al., "Noise and Military Service: Implications for Hearing Loss and Tinnitus," 2006, The National Academies Press, Washington, DC, pp. 1-320.

Kopke et al., "Candidate's thesis: enhancing intrinsic cochlear stress defenses to reduce noise-induced hearing loss," *Laryngoscope*, 2002; 112:1515-1532.

Kujawa and Liberman, "Adding insult to injury: cochlear nerve degeneration after "temporary" noise-induced hearing loss," *J Neurosci*, 2009; 29:14077-14085.

Lalive et al., "Glatiramer acetate in the treatment of multiple sclerosis: emerging concepts regarding its mechanism of action," *CNS Drugs*, 2011; 25:401-414.

Lampron et al., "Innate immunity in the CNS: redefining the relationship between the CNS and Its environment," *Neuron*, 2013; 78:214-232.

Le Prell et al., "Free radical scavengers, vitamins A, C, and E, plus magnesium reduces noise trauma," *Free Radic Biol Med*, 2007; 42:1454-1463.

Liu et al., "T cell independent mechanism for copolymer-1-induced neuroprotection," *Eur J Immunol*, 2007; 37:3143-3154.

McGee et al., "Recovery from noise-induced hearing loss is enhanced by the immunomodulator glatiramer acetate," Presented at the Association for Research in Otolaryngology 37th Annual Midwinter Meeting, Feb. 22-26, 2014, San Diego, CA. *Assoc. Res. Otolaryngol.*, 37:363, Abstract PS 573.

Miyao et al., "Acoustic trauma augments the cochlear immune response to antigen," *Laryngoscope*, 2008; 118:1801-1808.

Staton, "One, two, three, gone: Teva loses third patent on new Copaxone formula," FiercePharma, Sep. 1, 2016. Retrieved from the Internet on Sep. 2, 2016: <URL: http://www.fiercepharma.com/pharma/one-two-three-gone-teva-loses-third-patent-new-copaxone-formula?utm_medium=nl&utm_source=internal&mrkid=24091835&mkt_tok=eyJpIjoiWWpFME1XUTJZalkx-T0RFeiIsInQiOiJNbEljQUp5MFc4Z2N3ekU1dUJXeTIrdEVrMT-FjUWl0ZXA1VFwvY1Byc3p4TTZWZTdydHdhZ0RuNzE5TmV-nVklaYkhaWW1XZk5uaVE3b09lXC9CSnYwNThQcTlvZDNV-QmNNYVhMQUdlTU94NHFvPSJ9>; 5 pages.

Tornabene et al., "Immune cell recruitment following acoustic trauma," *Hear Res* 2006; 222:115-124.

U.S. Department of Veterans Affairs Annual Benefits Report, Fiscal Year 2012, Jun. 2013. Retrieved from the internet on Sep. 8, 2016: <URL: http://benefits.va.gov/REPORTS/abr/2012_abr.pdf>; 166 pages.

Yong, "Differential mechanisms of action of interferon-beta and glatiramer acetate in MS," *Neurology*, 2002; 59:802-808.

TREATMENT OF NOISE INDUCED HEARING LOSS

CONTINUING APPLICATION DATA

This application claims the benefit of U.S. Provisional Application Ser. No. 61/939,362, filed Feb. 13, 2014, which is incorporated by reference herein.

GOVERNMENT FUNDING

This invention was made with government support under N00014-14-1-0562, awarded by Office of Naval Research of the Department of Defense. The government has certain rights in the invention.

BACKGROUND

Permanent hearing loss associated with exposure to excessive entertainment, workplace and military noise not only diminishes an individual's quality of life, but also contributes significantly to the cost of both civilian and military service-related health care. The two most prevalent service-related disabilities in 2012 were tinnitus and hearing loss, accounting for more than one-third of disabilities among veterans. Active compensation benefits for all disabilities at the end of fiscal year 2012 amounted to over $44 billion dollars (U.S. Dept. of Veterans Affairs, Annual Benefits Report, Fiscal Year 2012). This was an increase from the 2006 report in which "disabilities of the auditory system . . . were the third most common type . . . among veterans", according to the National Research Council (NRC) 2006 report (Humes et al., 2006 *Noise and Military Service: Implications for Hearing Loss and Tinnitus*, National Research Council, The National Academies Press, Washington, D.C.), and " . . . monthly compensation payments to veterans with hearing loss as their major form of disability represented an annualized cost of some $660 million", again according to the NRC report (Humes et al., 2006 *Noise and Military Service: Implications for Hearing Loss and Tinnitus*, National Research Council, The National Academies Press, Washington, D.C.).

SUMMARY OF THE INVENTION

The present invention provides a method of preventing and/or treating noise-induced auditory impairments which includes administration of an effective amount of glatiramer acetate (also referred to herein as "GA") or a derivative thereof. The GA can be administered either prophylactically or therapeutically. In some embodiments the GA is administered both prophylactically and therapeutically.

In some aspects, the present invention provides methods of preventing, treating, and/or reducing noise induced hearing loss, the methods including the administration of glatiramer acetate or a derivative thereof. The glatiramer acetate or a derivative thereof may be administered prior to noise exposure and/or after noise exposure. In some embodiments of the methods, inner ear inflammation is reduced. In some embodiments, the methods may further include administration of at least one anti-oxidant. Exemplary antioxidants include acetyl-L-carnitine and D-methionine. In embodiments where an antioxidant is administered, the antioxidant may be administered prior to noise exposure and/or after noise exposure.

In some aspects, the present invention provides methods of preventing, treating, and/or reducing noise-induced inner ear trauma, the methods including the administration of glatiramer acetate or a derivative thereof. The glatiramer acetate or a derivative thereof may be administered prior to noise exposure and/or after noise exposure. In some embodiments of the methods, inner ear inflammation is reduced. In some embodiments, of the methods, the inner ear anatomy is protected. The inner ear anatomy includes the cochlear anatomy. Exemplary components of the cochlear anatomy includes hair cells, spiral ganglion neurons, and the synapses hair cells and spiral ganglion neurons. An exemplary feature of the cochlear anatomy that is made up of spiral ganglion neuron axons includes the eighth (VIII) cranial nerve. In some embodiments, the methods may further include administration of at least one anti-oxidant. Exemplary antioxidants include acetyl-L-carnitine and D-methionine. In embodiments where an antioxidant is administered, the antioxidant may be administered prior to noise exposure and/or after noise exposure.

In some aspects, the present invention provides methods of preventing or treating noise induced auditory impairment in a cochlea, the methods including the administration of glatiramer acetate or a derivative thereof. In some embodiments, the administration of GA regulates the production of at least one cytokine in the cochlea. In some embodiments, the regulated production of at least one cytokine may include the down-regulation of at least one pro-inflammatory cytokine Exemplary pro-inflammatory cytokines include IFN-$\gamma$, IL-2, IL-17, and TNF-$\alpha$. In some embodiments, the regulated production of at least one cytokine includes the up-regulation of at least one anti-inflammatory cytokine. An exemplary anti-inflammatory cytokine includes IL-4.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
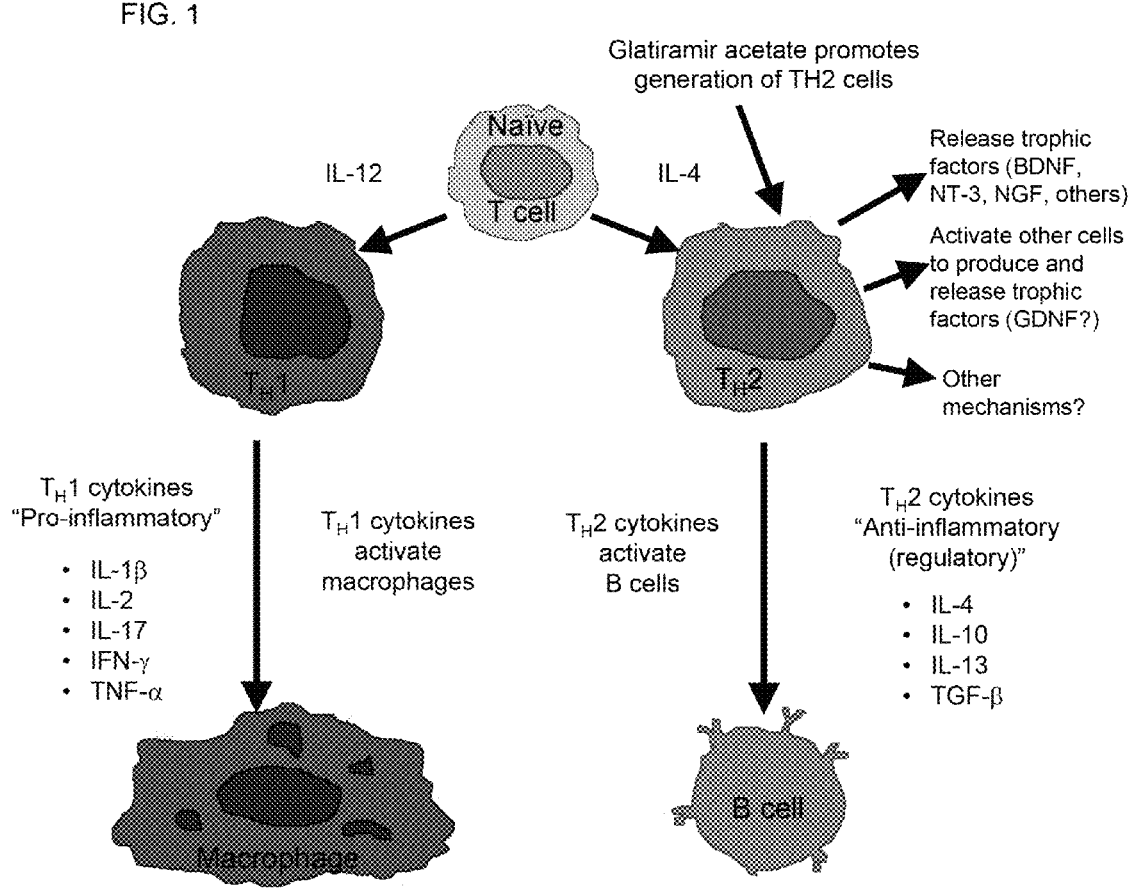
FIG. 1 shows a proposed molecular and humoral mechanism of glatiramer acetate (GA) action.

Although efforts to identify effective treatment protocols for noise-induced hearing loss (NIHL) have shown some promise in recent years (Campbell et al., 2007 *Hear Res* 226:92-103; Choi et al., 2008 *Free Radic Biol Med* 44:1772-1784; Kopke et al., 2002 *Laryngoscope* 112:1515-1532; Le Prell et al., 2007 *Free Radic Biol Med* 42:1454-1463), identifying treatment strategies that either prevent significant permanent hearing loss or rescue pre-existing hearing loss has been challenging. There is a critical need for the identification of protocols and methodologies (e.g., sensory cell regeneration and pharmaceutical protocols) that may effectively reduce the risk of NIHL and promote recovery from existing hearing loss. This is particularly relevant for military personnel, many of whom function in work environments with sound levels exceeding those recognized as biologically hazardous, such as the deck of aircraft carriers. Thus, this invention is particularly useful to address the hearing health of military personnel serving on aircraft carriers and in other particularly noisy service sectors.

The present invention provides a method of preventing and/or treating noise-induced auditory impairments which includes administration of an effective amount of glatiramer acetate (also referred to herein as "GA") or a derivative thereof. An effective amount of GA is the amount required to prevent, treat, and/or reduce one or more noise-induced auditory impairments. Effects of GA administration can be readily determined by one of skill in the art using physiological, morphological and molecular tools designed to quantitatively assess noise-induced auditory impairments such as hair cell and spiral ganglion neuronal populations. Such assays are known to one of skill in the art and include, but are not limited to, any of those described in the examples included herewith. Therapeutically effective concentrations and amounts may be determined by methodologies known to one of skill in the art; for example, by testing the compounds in known in vitro and in vivo systems, including any of those described herein.

"Noise-induced auditory impairments" include, but are not limited to, noise-induced hearing loss (NIHL) caused by acoustic trauma and gradually developing NIHL and typically results in damage to the inner ear, in particular damage to the cochlea. NIHL caused by acoustic trauma is often termed "noise-induced inner ear trauma" (NIIET) and is typically caused by exposure to excessive sound pressure. This form of NIHL commonly results from exposure to high-intensity sounds such as explosions, gunfire, a large drum hit loudly, and firecrackers, and a single exposure may be sufficient to cause trauma. Gradually developing NIHL is typically caused by repeated exposure to loud sounds over a period of time. Unlike NIHL from acoustic trauma, this form of NIHL does not occur from a single exposure to a high-intensity sound pressure level, but can be caused by multiple exposures to any source of excessive volume, such as home and vehicle stereos, concerts, nightclubs, excessive noise in the workplace, and personal media players.

The present invention focuses on a novel hearing loss prevention and treatment strategy involving a drug known to protect the central nervous system and the retina from injury by blocking the neurodegenerative consequences of inflammation. Glatiramer acetate (GA), an immunomodulator and neuroprotective agent (also known as Copolymer 1, Cop-1 or COPAXONE; CAS No. 147245-92-9; marketed by Teva Pharmaceuticals), is an FDA-approved drug for the treatment of multiple sclerosis. The mechanism of GA action is incompletely understood; however, a large number of anti-inflammatory compounds, as well as neurotrophic agents (FIG. 1) have been implicated as key elements in the mechanism underlying the drug's neuroprotective and neuroregenerative properties (Gentile et al., 2013 *J Neuroim-* mune *Pharmacol* 8:651-663; Lalive et al., 2011 *CNS Drugs* 25:401-414; Lampron et al., 2013 *Neuron* 78:214-232; Liu et al., 2007 *Eur J Immunol* 37:3143-3154). Studies of GA's protective actions in animal models of diseases such as Parkinson's and Alzheimer's, as well as efforts to identify signaling pathways that regulate the expression of anti-inflammatory agents known to cross the blood brain barrier, have also contributed to a more comprehensive understanding of the system (Carpintero et al., 2010 *Proc Natl Acad Sci USA* 107:17692-17697; Lalive et al., 2011 *CNS Drugs* 25:401-414; Lampron et al., 2013 *Neuron* 78:214-232; Liu et al., 2007 *Eur J Immunol* 37:3143-3154).

The present invention demonstrates that GA treatment reduces the amount of temporary and permanent hearing loss and/or accelerates the rate of recovery from temporary threshold shift (TTS). For example, the present invention demonstrates that GA improves auditory function following traumatizing noise exposure (Example 1). The present invention also demonstrates that recovery from NIHL is greater in treated subjects when compared to control subjects (Example 1). Without being bound by theory, it is believed that GA protects the cochlea, including sensory cells and spiral ganglion neurons (SGNs), from acoustic trauma.

The present invention includes methods of administering GA. The GA can be administered either prophylactically (administered prior to noise exposure) and/or therapeutically (administered after noise exposure). For example, the GA may be administered prior to noise exposure, for example, in a priming dose. Such administration prior to noise exposure may protect auditory function, for example, from inflammation-induced pathology precipitated by noise trauma. Alternatively, the GA may be administered after noise exposure. Such administration after noise exposure may rescue auditory function from inflammation-induced pathology precipitated by noise trauma and/or improves auditory function following traumatizing noise exposure. In some embodiments the GA is administered both prophylactically and therapeutically.

The present invention provides methods of preventing, treating, and/or reducing noise induced hearing loss, the methods including the administration of glatiramer acetate or a derivative thereof.

The present invention provides methods of preventing, treating, and/or reducing noise-induced inner ear trauma, the methods including the administration of glatiramer acetate or a derivative thereof.

The present invention provides methods of preventing or treating noise induced auditory impairment in a cochlea, the methods including the administration of glatiramer acetate or a derivative thereof. In some embodiments, the administration of GA regulates the production of at least one cytokine in the cochlea.

As used herein a GA derivative may include, for example, any salt, ester, ether, polymorph, metabolite, pure form, particle, isomer, mixture of isomers, complex, or combination thereof provided it maintains the function of GA as described herein. That is, a derivative of GA protects and/or rescues auditory function associate with noise-induced auditory impairments.

In some aspects, the present invention also provides methods of preventing, treating, and/or reducing noise induced hearing loss, methods of preventing, treating, and/or reducing noise-induced inner ear trauma, and methods of preventing or treating noise induced auditory impairment in a cochlea, the methods including the administration of a neuroprotective agent other than GA and/or an immuno-modulator other than GA.

Inflammation resulting from overexposure to noise is generally recognized as a proximate cause of sound-induced permanent hearing loss. Inner ear inflammation occurs following acoustic overstimulation presumably as a direct consequence of trauma-enhanced pro-inflammatory cytokine expression (Fujioka et al., 2006 *J Neurosci Res* 83:575-583; Tornabene et al., 2006 *Hear Res* 222:115-124). The inflammatory response is presumed to be one cause of sound-induced permanent hearing loss (Miyao et al., 2008 *Laryngoscope* 118:1801-1808). Synaptopathy and delayed spiral ganglion cell loss have also been observed following noise-induced temporary loss of sensitivity in mice (Kujawa and Liberman, 2009 *J Neurosci* 29:14077-14085). GA has general anti-inflammatory properties and advantageously its anti-inflammatory actions reduce inner ear inflammation following noise exposure (Example 3). Thus, administration of GA pharmaceutically regulates the natural production and release of anti-inflammatory chemicals to both prevent and treat NIHL.

In some embodiments, the methods of the present invention reduce inner ear inflammation. Such methods include the administration of GA which regulates the production of at least one cytokine. In some embodiments, the regulation of the production of cytokines occurs in the inner ear. In exemplary embodiments, the regulation of the production of cytokines occurs in the cochlea. Cytokines are small signaling proteins that are produced and released by a broad range of cells, including immune cells like macrophages, B lymphocytes, T lymphocytes and mast cells, as well as endothelial cells, fibroblasts, and various stromal cells. Cytokines include, without limitation, chemokines, interferons, interleukins, lymphokines, and tumour necrosis factor, and are important in many cellular functions including inflammation. The production of at least one cytokine may include the down-regulation of at least one pro-inflammatory cytokine, the up-regulation of at least one anti-inflammatory cytokine, or a combination thereof.

The regulated production of at least one cytokine may include down-regulation of at least one pro-inflammatory cytokine A pro-inflammatory cytokine is a cytokine which promotes inflammation. Non-limiting examples of pro-inflammatory cytokines include, without limitation, interferon gamma (IFN-γ), Interleukin 2 (IL)-2, IL-17, tumor necrosis factor alpha (TNF-α), IL-1, IL-6, and IL-8. In embodiments where at least one pro-inflammatory cytokine is down-regulated, the pro-inflammatory cytokine may be selected from IFN-γ, IL-2, IL-17, or TNF-α.

The regulated production of at least one cytokine may include up-regulation of at least one anti-inflammatory cytokine. An anti-inflammatory cytokine is a cytokine which reduces inflammation. Non-limiting examples of anti-inflammatory cytokines include, without limitation, IL-4, IL-1ra, and IL-10. In embodiments where at least one anti-inflammatory cytokine is up-regulated, the anti-inflammatory cytokine may be IL-4.

In some embodiments, the methods of the invention protect the inner ear anatomy. The inner ear is the innermost part of the vertebrate ear and is mainly responsible for sound detection and balance. In mammals, inner ear anatomy consists of the two main functional parts: the cochlea, dedicated to hearing; and the vestibular system dedicated to balance. The cochlear anatomy includes many small structures including, without limitation, hair cells and spiral ganglion neurons. A spiral ganglion neuron has its cell body in the spiral ganglion, its dendrites making synaptic contact with the base of hair cells, and its axon bundled together with other spiral ganglion neuron axons to form the auditory portion of the eighth (VIII) cranial nerve. In embodiments, protecting the inner ear anatomy includes protecting the cochlear anatomy. In some embodiments, the cochlear anatomy is selected from a hair cell, a spiral ganglion neuron, and/or the synapse between the hair cell and the spiral ganglion neuron. In exemplary embodiments, the spiral ganglion neuron comprises an eighth (VIII) cranial nerve.

In some embodiments, the methods of the instant invention further include administration of at least one antioxidant. It is widely recognized that oxidative stress resulting from increased levels of reactive oxygen species (ROS) and free radicals contributes to hair cell death and associated pathology observed following acoustic trauma (Henderson et al., 2006 *Ear Hear* 27:1-19; Le Prell et al., 2007 *Free Radic Biol Med* 42:1454-1463). In addition, antioxidant therapy with acetyl-L-carnitine and/or D-methionine protect sensory cells from metabolic defects resulting from acoustic trauma (Campbell et al., 2007 *Hear Res* 226:92-103; Choi et al., 2008 *Free Radic Biol Med* 44:1772-1784; Kopke et al., 2002 *Laryngoscope* 112:1515-1532). Without being bound by theory, it is believed that GA and antioxidant therapy will operate cooperatively, perhaps synergistically, to prevent or reduce hearing loss following exposure to traumatizing noise leading to more complete protection of the inner ear from acoustic trauma than that observed with GA alone. An antioxidant may be any molecule that inhibits the oxidation of other molecules. Antioxidants are typically oxidized themselves and therefore often act as reducing agents such as thiols, ascorbic acid, or polyphenols. Non-limiting examples of antioxidants include acetyl-L-carnitine, D-methionine, ascorbic acid (vitamin C), glutathione, lipoic acid, uric acid, carotenes, retinol (vitamin A), $\alpha$-tocopherol (vitamin E), ubiquinol (coenzyme Q), eugenol, beta-carotene, selenium, zinc, and enzymes such as catalase, superoxide dismutase and various peroxidases. The antioxidant may be hydrophilic (soluble in water), lipophilic (soluble in lipids), or non-polar. Hydrophilic antioxidants include, without limitation, ascorbic acid (vitamin C), glutathione, lipoic acid, uric acid. Lipophilic antioxidants include, without limitation, carotenes, retinol (vitamin A), $\alpha$-tocopherol (vitamin E), and ubiquinol (coenzyme Q). Nonpolar antioxidants include eugenol. In some embodiments, antioxidant therapy includes administering at least one of acetyl-L-carnitine and D-methionine. The antioxidant may be administered prior to noise exposure, after noise exposure, or both before and after noise exposure. The antioxidant may be administered together with GA or the antioxidant may be administered as an independent composition.

With the methods described herein, GA may be administered as a composition including GA (and optionally an antioxidant) and a pharmaceutically acceptable carrier. "Pharmaceutically acceptable" refers to a pharmacologically inactive substance that is compatible with the other ingredients of the composition, and not deleterious to the recipient thereof. Typically, the composition includes a pharmaceutically acceptable carrier when the composition is used as described herein. In some embodiments, a composition may include additional active ingredients.

A composition may be prepared by methods well known in the art of pharmacy. The compositions disclosed herein may be formulated in pharmaceutical preparations in a variety of forms adapted to the chosen route of administration. A formulation may be solid or liquid. Administration may be systemic or local. Examples of routes of administration include parenteral (e.g., intravenous, intradermal, subcutaneous, intraperitoneal, intramuscular), enteral (e.g., oral), and topical (e.g., epicutaneous, inhalational, transmucosal, transdermal) administration.

A composition intended for oral delivery may include an inert diluent or an edible carrier. For the purpose of oral therapeutic administration, the active agent can be incorporated with excipients and used in the form of tablets, troches, or capsules. Oral compositions can also be prepared using a fluid carrier. Pharmaceutically compatible binding agents can be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

A composition for use in topical administration may be formulated into many types of vehicles. Topical delivery may be accomplished, for example, with a transdermal patch. One example is EMSAM, the transdermal patch form of selegiline, approved in February 2006 by the US Food and Drug Administration for use in treating major depression. The once a day patch works by delivering selegiline through the skin and into the bloodstream and comes in three sizes that deliver 6, 9, or 12 mg of selegiline per 24 hours. In other embodiments, an active agent may be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed, examples include nanospheres and nanocapsules) that can be used as delivery vehicles to deliver such ingredients to skin.

As used herein "treating" or "treatment" can include therapeutic and/or prophylactic treatments. "Treating a disorder," as used herein, is not intended to be an absolute term. Treatment may lead to an improved prognosis or a reduction in the frequency or severity of symptoms. Desirable effects of treatment include preventing occurrence or recurrence of disease or condition, alleviation of symptoms, diminishment of any direct or indirect pathological consequences of the disease or condition, decreasing the rate of disease or condition progression, amelioration or palliation of the disease or condition state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only about 90%, about 80%, about 70%, about 60%, about 50%, about 40%, about 30%, about 20%, about 10%, about 5% or 1% as frequent or severe as symptoms experienced by an untreated individual with the disorder.

As used herein, the term "subject" includes, but is not limited to, humans and non-human vertebrates. In preferred embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, mice, guinea pigs, hamsters, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

In several places throughout the application, guidance is provided through lists of examples, which examples can be used in various combinations. In each instance, the recited list serves only as a representative group and should not be interpreted as an exclusive list.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Treatment with the Glatiramer Acetate Prevents or Reduces Hearing Loss in Mice Following Exposure to Traumatizing Noise Experimental Design To determine if the glatiramer acetate (GA) prevents or reduces hearing loss in mice following exposure to traumatizing noise, following determination of baseline acoustic thresholds (i.e., pre-noise exposure thresholds), hearing sensitivity and input-output relationships was assessed during the post-noise exposure period using auditory evoked brainstem responses (ABRs) and distortion product otoacoustic emissions (DPOAEs); DPOAEs were studied using the same protocol as in ABR-based studies to separate findings associated with neural and sensory outcomes. Responses to tone burst stimuli was acquired immediately following noise exposure, daily during the early post-exposure period, and intermittently thereafter for six (6) months to generally assess the long-term outcome of exposure to traumatizing noise in CBA mice. Morphological correlates of final treatment outcomes, including sensory and support cell (cytocochleograms), synapses between hair cells and spiral ganglion dendrites, and SGN survival estimates, was made at the end of the acute phase (2 months following noise exposure) or at 6 months to assess long-term outcomes.

The traumatizing noise used in CBA mouse studies was an octave band of white noise centered on 11.3 kHz and was presented at 109 dB SPL for 30 min. Because of well-documented differences in the abilities of males and females to mount inflammatory responses, both males and females were included in this investigation.

In mice, GA (100 mg/kg) was administered following two treatment strategies. In Group 1, GA was administered in sequential doses one month and one week prior to noise exposure (the "protection" approach), with supplementary doses on a daily basis for the first 4 days following noise exposure and again on the $7^{th}$ and $14^{th}$ post-exposure days in mice, to determine if GA can prevent permanent hearing loss associated with traumatizing noise. In Group 2, GA was administered only during the post-noise exposure period in an effort to determine if GA can rescue hearing following acute trauma. In a subset of animals, GA was administered prior to noise exposure and then daily for the first ten post-exposure days. Complete Freund's adjuvant will be used to deliver the first dose of the agent to determine if GA actions might be potentiated (boosted) when delivered in an emulsified form in a separate group of mice.

Figure 2:
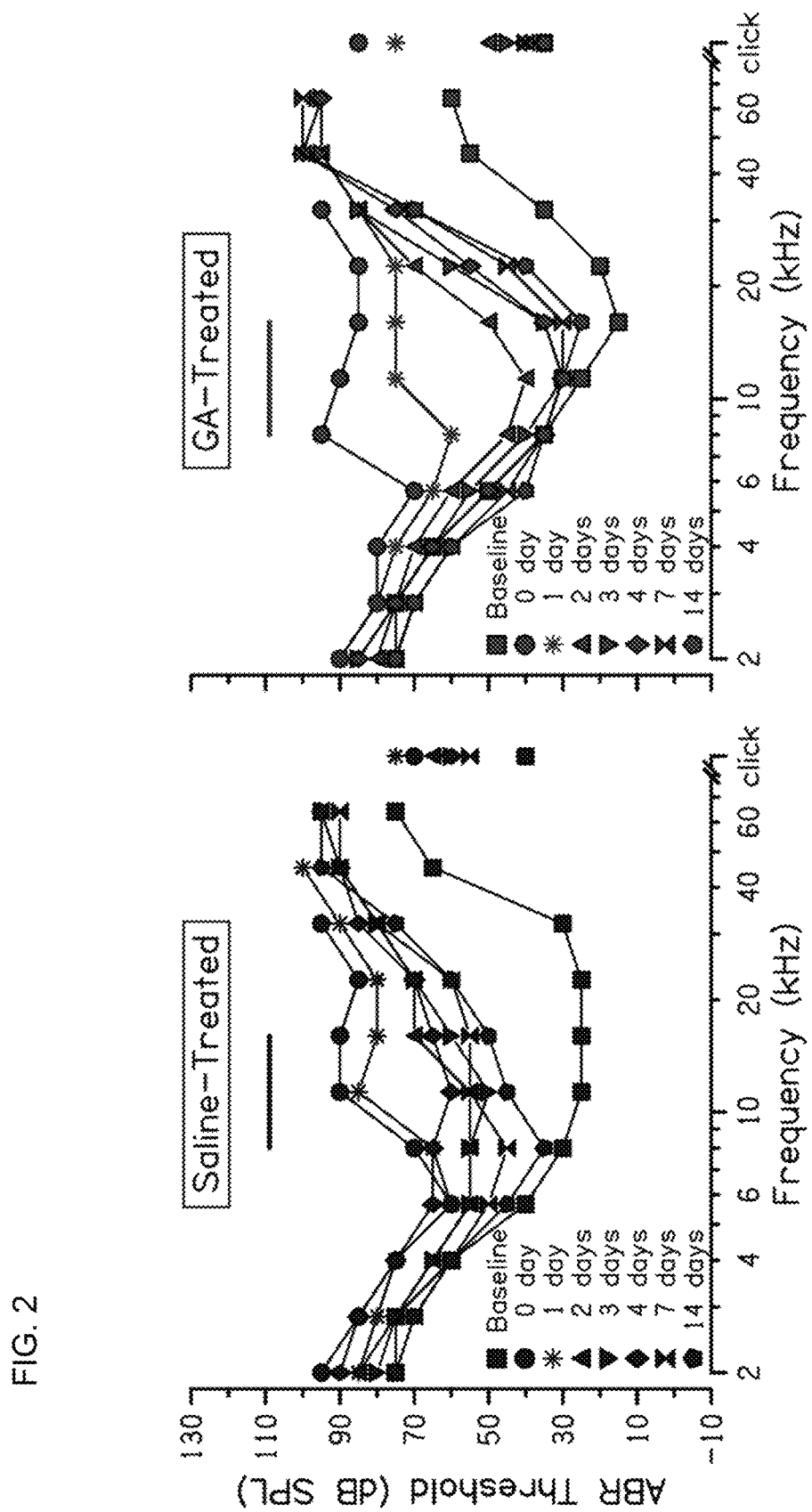
FIG. 2 shows a pre-(baseline) and post-noise exposure auditory brainstem response (ABR) threshold-frequency curves acquired over the first 14 days following acute noise trauma (day 0) in a saline-treated mouse and a GA-treated mouse.

An example of findings associated with this experimental design is shown in FIG. 2, in which families of ABR threshold-frequency curves (audiograms) generated by tracking sensitivity according to the "protection" protocol reviewed above in a GA-treated animal (right panel) and a saline-treated control (left panel) that were exposed to noise simultaneously are shown.

With this example, to determine if treatment with GA alone reduces the amount of temporary and permanent hearing loss and/or accelerates the rate of recovery from temporary threshold shift (TTS), groups of mice received GA or saline and were evaluated as described above.

Figure 3:
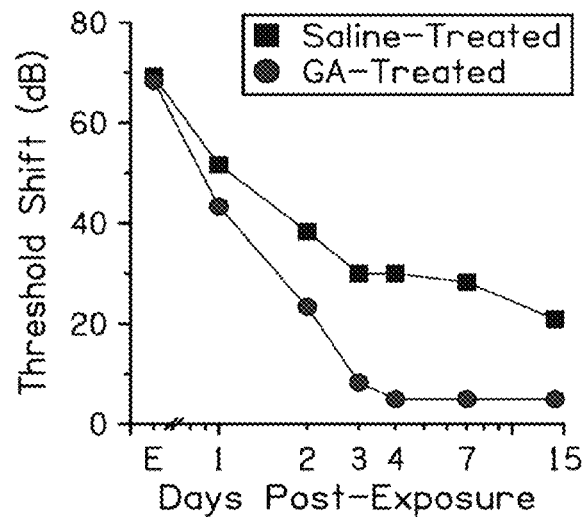
FIG. 3 shows changes in ABR sensitivity at 11.3 kHz over a two week period following noise exposure (E).
Figure 4:
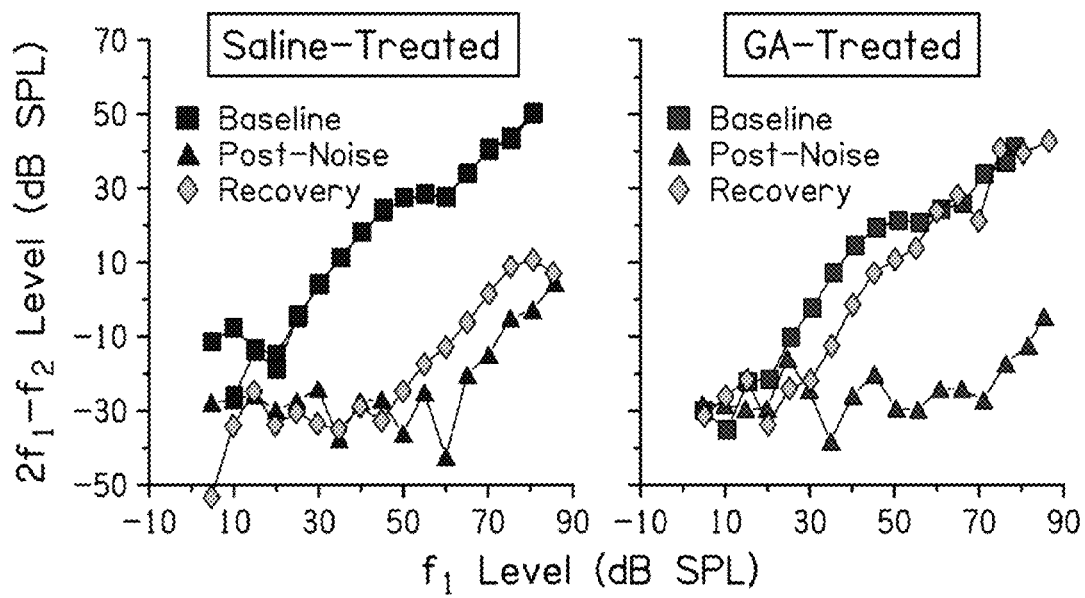
FIG. 4 shows significant recovery in distortion product otoacoustic emissions (DPOAEs) from noise exposure in a GA-treated mouse (right) compared to a saline-treated control (left) two weeks after exposure. F2=11.3 kHz, f2/f1=1.2, 12=11-10 dB.

Thresholds were elevated significantly, ~60-70 dB in the vicinity of 11.3 kHz and higher frequencies, immediately following noise exposure in both groups. Recovery from NIHL was nearly complete in the GA-treated mouse for frequencies at and immediately above the center-frequency (CF) of the traumatizing noise, while recovery in the saline-treated animal was less complete. This outcome is more clearly demonstrated by comparing the time course of recovery from NIHL in the GA- and saline-treated animals at the noise band's CF, 11.3 kHz (FIG. 3). In addition, nearly complete recovery of outer hair cell (OHC) function was observed in the form of DPOAE input-output curves representing a GA-treated mouse (right panel) relative to a saline-treated (left panel) animal 14 days following noise exposure (FIG. 4).

Figure 5:
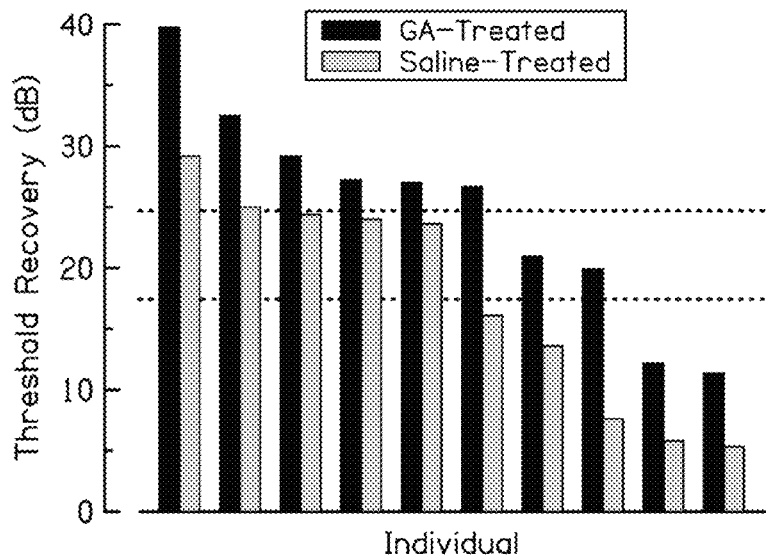
FIG. 5 shows GA-treated mice consistently show greater recovery from threshold elevations induced by noise exposure than saline-treated controls. Means are shown as dotted lines.

The overall findings from this example are shown in FIG. 5. The magnitude of threshold recovery following noise exposure, computed as the overall average recovery in dB across all stimulus frequencies studied, is rank-ordered across individuals in FIG. 5, and ranged from approximately 40 dB to approximately 10 dB in GA-treated mice, and <30 dB to approximately 5 dB in saline-treated controls. The total extent of recovery following exposure was nearly 25 dB in the GA cohort and approximately 17 dB in control animals. This example indicates that recovery is significantly enhanced by GA treatment alone (P<0.05). This example indicates that GA prevents or reduces hearing loss in mice following exposure to traumatizing noise, and that GA-induced protection is generally efficacious.

Example 2

Combined Actions of Glatiramer Acetate and Antioxidant Therapy Will Operate Synergistically to Prevent or Reduce Hearing Loss in Mice Following Exposure to Traumatizing Noise To determine if additional protection via an alternate mechanism (i.e., reducing oxidative stress) is achievable, separate groups of mice will receive GA plus acetyl-L-carnitine and D-methionine, antioxidants that have been previously shown to partially protect animals from acute NIHL. In the pre-exposure group, Group 3, acetyl-L-carnitine and D-methionine will be administered at a dose of 100 mg/kg and 200 mg/kg respectively according to the following dosing schedule: twice daily beginning 48 hrs before, noise exposure, 1 hr before exposure, and 1 hr post-noise exposure, then twice daily for the following two days (Campbell et al., 2007 Hear Res 226:92-103; Choi et al., 2008 Free Radic Biol Med 44:1772-1784; Kopke et al., 2002 Laryngoscope 112:1515-1532), along with GA administration as described above for Group 1. In the post-exposure group, Group 4, acetyl-L-carnitine and D-methionine will be administered at doses of 100 mg/kg and 200 mg/kg respectively according to the following dosing schedule: 1 hr after noise exposure, then twice daily for the following two days, along with GA administration as described for Group 2. The rationale underlying this experimental design is that exposure to increased levels of ROS and free radicals, as well as the development of inflammatory responses following noise-induced trauma combine to produce hearing loss.

Example 3

Glatiramer Acetate Reduces Inner Ear Inflammation in Noise Exposed Animals

To determine if GA affects cytokine expression, groups of mice received GA as described above, and cytokine expression was evaluated via RT-PCR.

Figure 6:
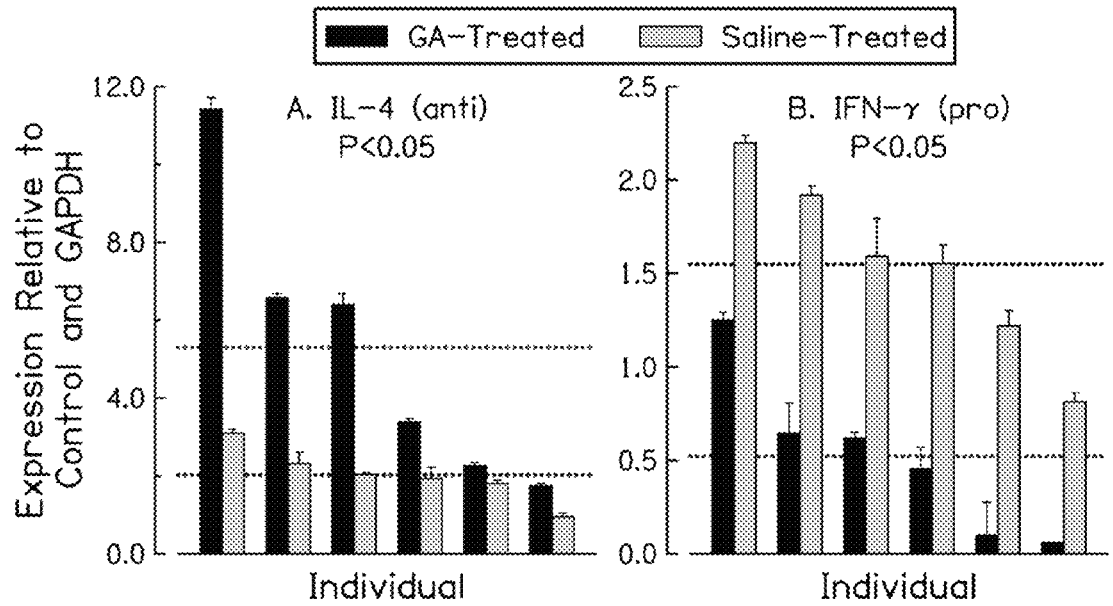
FIG. 6 shows anti- and pro-inflammatory cytokine expression in mice 10 days following noise exposure (Group 1) is consistent with the anti-inflammatory action of GA. Horizontal lines denote average values for each group.
Figure 7:
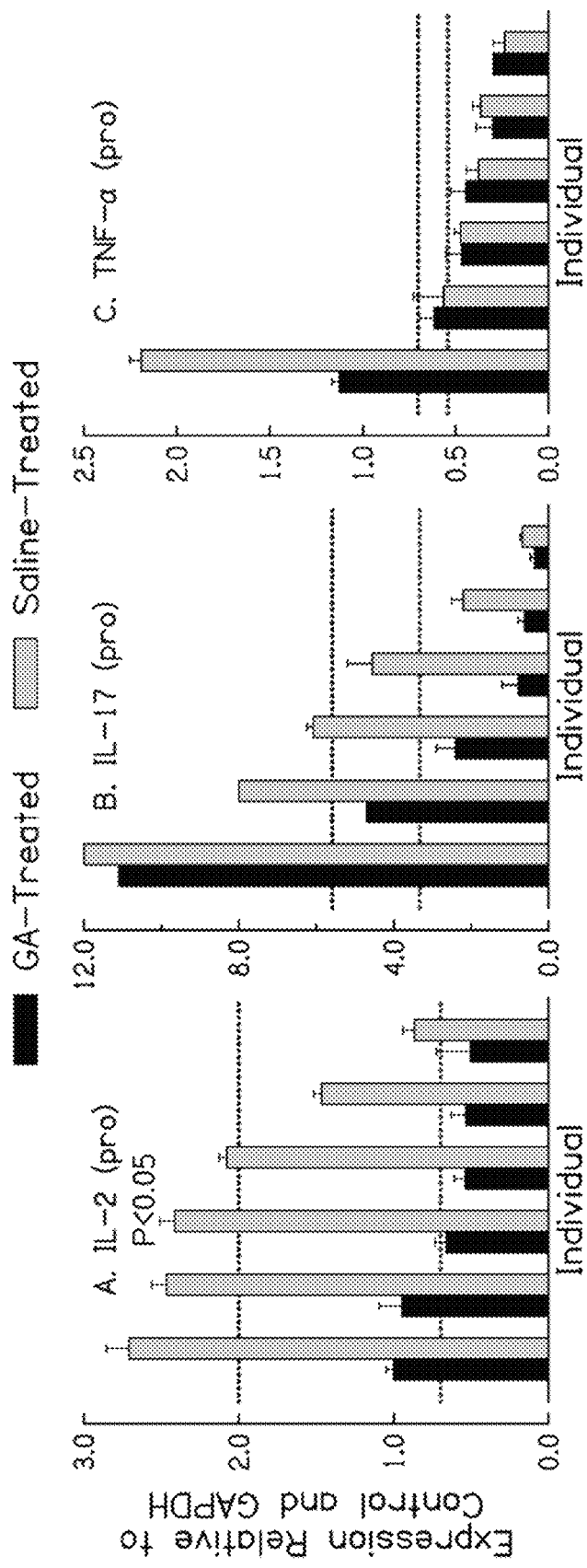
FIG. 7 shows pro-inflammatory cytokine expression is generally reduced in mice 10 days following noise exposure (Group 1) and is consistent with the anti-inflammatory action of GA. Horizontal lines denote average values for each group.

Using RT-PCR, the effects of GA on cytokine expression in the cochlea, specifically those mediators associated with pro- or anti-inflammatory activity, was established. Following GA injections, sera was assayed to determine if the immune response had shifted from a cellular to humoral response. qRT-PCR findings based on analysis of spleen tissues show that expression of pro-inflammatory cytokines (e.g., IL-2, IL-17, interferon-gamma, and TNF-alpha) was down-regulated, along with a coincident up-regulation of mediators associated with Th2 and Th3 responses such as IL-4 and TGF-$\beta$. Expression of anti-inflammatory cytokine, IL-4, was upregulated (2.6-fold greater than controls) in animals treated with GA and interferon-gamma was down-regulated (66% reduction re controls) in GA-treated animals (FIG. 6). Expression of pro-inflammatory cytokines, IL-2, IL17, and TNF-$\alpha$ was also down-regulated in GA-treated animals (FIG. 7).

Figure 8:
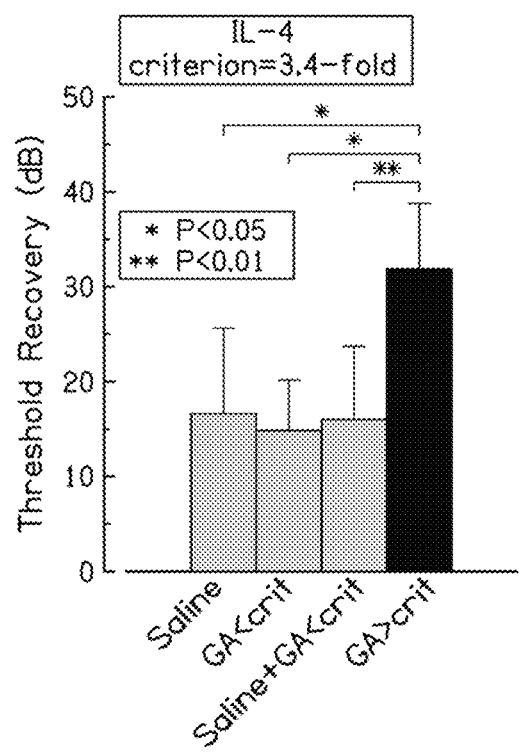
FIG. 8 shows overall threshold recovery from noise-induced hearing loss is significantly greater for mice in which glatiramer acetate (GA) induced at least a 3.4-fold increase in IL-4 expression (criterion, "crit") than in saline-treated controls and GA-treated mice in which IL-4 expression was below the criterion level.

Overall threshold recovery from NIHL was examined in mice having upregulated anti-inflammatory cytokines Threshold recovery from NIHL was significantly greater in mice in which in IL-4 expression was increased above criterion level (an increase of at least 3.4-fold IL-4 expression) relative to saline-treated controls and relative to GA-treated mice in which IL-4 expression was below the criterion level (FIG. 8).

Figure 9:
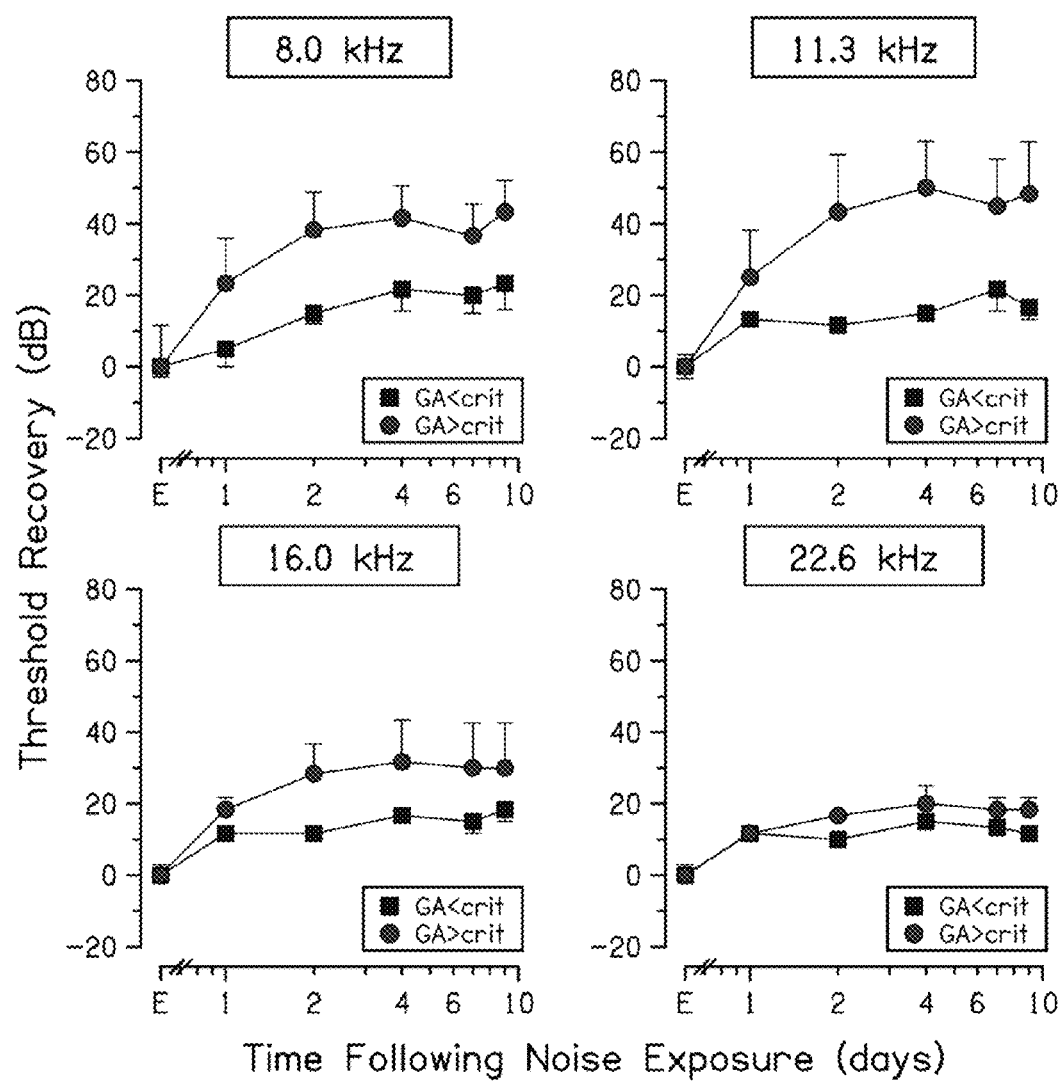
FIG. 9 shows recovery of thresholds during the first 10 days following noise exposure (E) at three stimulus frequencies within the noise band (8.0, 11.3 and 16.0 kHz) and one frequency outside the noise band (22.6 kHz) for mice in which glatiramer acetate (GA) induced at least a 3.4-fold increase in IL-4 expression (criterion, "crit") than in GA-treated mice in which IL-4 expression was below the criterion level.

Threshold recovery following noise exposure was examined in mice having upregulated anti-inflammatory cytokines (FIG. 9). During the first 10 days following exposure, threshold recovery following noise exposure was greater in mice in which in IL-4 expression was increased above criterion level (an increase of at least 3.4-fold IL-4 expression) relative to saline-treated controls and relative to GA-treated mice in which IL-4 expression was below the criterion level for stimulus frequencies within the noise band (8.0, 11.3 and 16.0 kHz).

This example indicates that pro-inflammatory cytokine expression is diminished and anti-inflammatory cytokines is enhanced following noise exposure in GA-treated animals relative to vehicle-treated control animals.

Example 4

Combined Actions of Glatiramer Acetate and Antioxidant Therapy Will Operate Synergistically to Prevent or Reduce Hearing Loss in Guinea Pigs Following Exposure to Traumatizing Noise To determine if additional protection via an alternate mechanism (i.e., reducing oxidative stress) is achievable, separate groups of guinea pigs will receive GA plus acetyl-L-carnitine and D-methionine, antioxidants that have been previously shown to partially protect animals from acute NIHL. In the pre-exposure group, Group 3, acetyl-L-carnitine and D-methionine will be administered at a dose of 325 mg/kg and 600 mg/kg respectively according to the following dosing schedule: twice daily beginning 48 hrs before noise exposure, 1 hr before exposure, and 1 hr post-noise exposure, then twice daily for the following two days (Campbell et al., 2007 Hear Res 226:92-103; Choi et al., 2008 Free Radic Biol Med 44:1772-1784; Kopke et al., 2002 Laryngoscope 112:1515-1532), along with GA administration as described above for Group 1. In the post-exposure group, Group 4, acetyl-L-carnitine and D-methionine will be administered at doses of 325 mg/kg and 600 mg/kg respectively according to the following dosing schedule: 1 hr after noise exposure, then twice daily for the following two days, along with GA administration as described for Group 2. The rationale underlying this experimental design is that exposure to increased levels of ROS and free radicals, as well as the development of inflammatory responses following noise-induced trauma combine to produce hearing loss.

Example 5

Operational Effectiveness of Glatiramer Acetate in a Naval Setting

To determine the operational effectiveness of GA treatment in a realistic naval scenario, animals will be exposed to actual and/or recorded turbofan engine noise produced by today's high performance tactical aircraft. Experiments may be conducted in situ (deck of aircraft carrier) and/or in a simulated aircraft carrier environment to determine the vulnerability of crew members to jet engine noise.

This investigation will be carried out using outbred Guinea pigs in an effort to determine the influence of genetic polymorphisms on study outcomes. An additional advantage of studying the Guinea pig is related to the fact that Guinea pigs have auditory attributes more like those of humans.

Hearing, and recovery from noise-induced hearing loss, will be evaluated physiologically in exposed animals, along with morphological correlates, in accordance with protocols as described in more detail in the previous examples. Specifically, the efficacy of treatment strategies will be evaluated physiologically in noise-exposed animals during the early and long term periods following noise exposure using the strategy outlined below.

Procedurally, half of the study group will be treated initially with 500 µg/kg GA suspended in Freund's adjuvant, then daily injections of 500 µg/kg GA (without adjuvant) using a modification of the "protection" protocol proposed above and the remaining animals will serve as controls and receive equivalent injections of vehicle. Recovery from NIHL will be evaluated physiologically during the early period following noise exposure, as well as 3 months following exposure using the strategy outlined above.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of reducing noise induced hearing loss, the method comprising the administration of glatiramer acetate.

2. The method of claim 1, wherein inner ear inflammation is reduced.

3. The method of claim 1, wherein the glatiramer acetate is administered prior to noise exposure and/or after noise exposure.

4. The method of claim 1, further comprising the administration of at least one anti-oxidant.

5. The method of claim 4, wherein the antioxidant comprises acetyl-L-carnitine and/or D-methionine.

6. The method of claim 4, wherein the antioxidant is administered prior to noise exposure and/or after noise exposure.

7. A method of reducing noise-induced inner ear trauma, the method comprising the administration of glatiramer acetate.

8. The method of claim 7, wherein inner ear inflammation is reduced.

9. The method of claim 7, wherein inner ear anatomy is protected.

10. The method of claim 9, wherein the inner ear anatomy comprises the cochlear anatomy.

11. The method of claim 10, wherein the cochlear anatomy is selected from a hair cell, a spiral ganglion neuron, or a synapse between a hair cell and a spiral ganglion neuron.

12. The method of claim 11, wherein the spiral ganglion neuron comprises an eighth (VIII) cranial nerve.

13. The method of claim 7, wherein the glatiramer acetate is administered prior to noise exposure and/or after noise exposure.

14. The method of claim 7, further comprising the administration of at least one anti-oxidant.

15. The method of claim 14, wherein the antioxidant comprises acetyl-L-carnitine and/or D-methionine.

16. A method of reducing noise induced auditory impairment in a cochlea, the method comprising the administration of glatiramer acetate, wherein the administration regulates the production of at least one cytokine in the cochlea, wherein the regulated production of at least one cytokine comprises down regulation of at least one pro-inflammatory cytokine selected from IFN-γ, IL-2, IL-17, or TNF-α and/or up-regulation of at least one anti-inflammatory cytokine selected from IL-4 or TGF-β.

17. The method of claim 14, wherein the antioxidant is administered prior to noise exposure and/or after noise exposure.

18. The method of claim 17, wherein the glatiramer acetate is administered prior to noise exposure and/or after noise exposure.

19. The method of claim 17, further comprising the administration of at least one anti-oxidant.

20. The method of claim 19, wherein the antioxidant comprises acetyl-L-carnitine and/or D-methionine.

* * * * *

UNITED STATES PATENT AND TRADEMARK OFFICE
CERTIFICATE OF CORRECTION

PATENT NO. : 9,763,992 B2  
APPLICATION NO. : 14/621978  
DATED : September 19, 2017  
INVENTOR(S) : Edward J. Walsh Page 1 of 1

It is certified that error appears in the above-identified patent and that said Letters Patent is hereby corrected as shown below:

In Column 14, Line 56, Claim 18, delete "The method of claim 17" and replace with --The method of claim 16--.

In Column 14, Line 59, Claim 19, delete "The method of claim 17" and replace with --The method of claim 16--.

Signed and Sealed this  
Thirtieth Day of October, 2018

Andrei Iancu  
*Director of the United States Patent and Trademark Office*